United States Patent [19]

Behme et al.

[11] 4,060,440

[45] Nov. 29, 1977

[54] METHOD OF SPECIMEN PREPARATION

[75] Inventors: Werner Behme, Walldorf; Manfred Berleth, Eppelheim, both of Germany

[73] Assignee: R. Jung AG Fabrik fur Prazisionsapparate, Heidelberg, Germany

[21] Appl. No.: 804,197

[22] Filed: June 6, 1977

Related U.S. Application Data

[60] Continuation of Ser. No. 625,961, Oct. 28, 1975, abandoned, which is a division of Ser. No. 453,142, March 20, 1974, abandoned.

[51] Int. Cl.² .............................................. B32B 31/18
[52] U.S. Cl. .................................. 156/154; 83/915.5; 90/11 C
[58] Field of Search ............... 156/153, 154, 230, 241, 156/344, 250; 83/915.5; 90/11 C, 19; 51/323, 326; 427/4

[56] References Cited

U.S. PATENT DOCUMENTS

| | | | |
|---|---|---|---|
| 3,763,611 | 10/1973 | Duhring | 51/323 |
| 3,877,122 | 4/1975 | Wilson | 51/323 |

FOREIGN PATENT DOCUMENTS

| | | | |
|---|---|---|---|
| 456,164 | 4/1949 | Canada | 83/915.5 |

OTHER PUBLICATIONS

*Van Nostrand Scientific Encyclopedia*, 4th Ed. (1968), Van Nostrand Co., Princeton, New Jersey, pp. 922, 1127–1129.

*Primary Examiner*—Charles E. Van Horn
*Assistant Examiner*—Jerome W. Massie
*Attorney, Agent, or Firm*—Howard R. Berkenstock, Jr.

[57] ABSTRACT

The invention pertains to method and apparatus for specimen preparation, in conjunction with which at least one specimen surface is produced on a test piece embedded, if required, in a casting-resin mounting medium through chip or slice removal of material and wherein the examined specimen surface is milled; especially, a method for the preparation of hard objects, and/or objects exhibiting differential hardness over the specimen surface, for electron scan microscopic and X-Ray studies. The invention further includes apparatus for preparing a specimen for examination which includes a milling head.

1 Claim, 1 Drawing Figure

U.S. Patent
Nov. 29, 1977
4,060,440
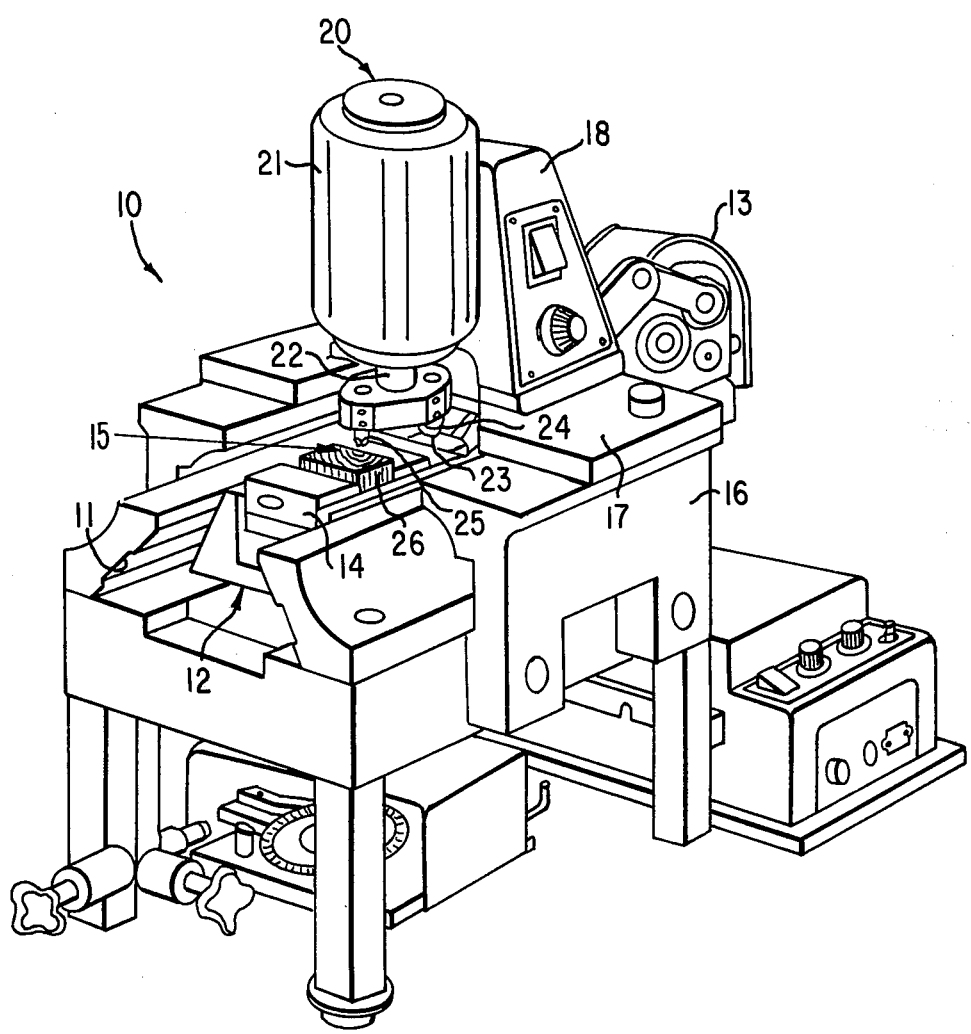

METHOD OF SPECIMEN PREPARATION

This is a continuation of application Ser. No. 625,961 filed Oct. 28, 1975, now abandoned, which is a division of application Ser. No. 453,142, filed Mar. 20, 1974, now abandoned.

BACKGROUND OF THE INVENTION

In order to be able to study hard objects such as metals, synthetics, fiber materials, multicomponent materials, cortex and bone substances, essentially free from artifacts, use is often made of the techniques of cross-cutting, microtome processing, or surface grinding followed by polishing. For these preparation methods, the embedding of the specimens in casting-resin block mounting media is required. In such methods, the hardness of the mounting media must be coordinated with the hardness of the given specimen. Such a coordination, however, is frequently only roughly achievable approximately, for instance because for a required slice-thickness, or when polishing, a selected average hardness of the overall specimen surface must be made.

The techniques heretofore applied in such preparations, which are dependent overall on the most extensive possible optimal coordination of the hardness of the block mounting-medium to the specimen hardness, have proven to this extent to be inadequate and in need of improvement. This is especially true for incident illumination as it requires the most extensively smooth, roughness-free specimen surfaces possible. Surface qualities of the required type are to be achieved with the use of known techniques of preparation, although generally involving time and money in further treatment. These techniques fail to a great extent, however, in multiphase systems, wherein strong hardness-differences occur in the specimen surface. Such an example can be only inadequately resolved with known preparation methods. Specifically, the soft pulp of a tooth, which is surrounded by the harder tooth enamel is such an example. Roughness-free cutting surfaces cannot be achieved. Instead, crushing and deformation occur in the specimen areas which exhibit only slight hardness. On polishing, pores and cavities present in the material are clogged with polishing compound. Test pieces prepared in such a manner are only conditionally suitable for incident illumination studies.

DESCRIPTION OF THE DRAWING

The FIGURE is a perspective view of apparatus embodying the invention.

SUMMARY OF THE INVENTION

Accordingly, it is proposed with the present invention to afford an improved method for the preparation of specimen surfaces, especially for electron scan microscope and X-Ray studies, in conjunction with which this method must guarantee a specimen quality adequate for the requirements of the subsequent specimen studies, even where strong specimen hardness differences are involved in the slide surface. Furthermore, a device for the implementation of this method will be proposed.

From the standpoint of technical method, the task before us is resolved in such a manner that in conjunction with the specimens to be studied, a mirror-smooth and most roughness-free possible specimen surface is achieved, through removal of material by milling. The material removal, in so doing, can be undertaken in several sequential layers of a given predetermined thickness, or in stages in a predetermined layer-thickness.

The preparation technique presently indicated is appropriate in a special degree for the preparation of test pieces for studies in incident illumination. Within the scope of the method proposed, however, success is also achieved in the production of the thinnest layer or slice specimens for microscopie studies in transmitted light, in such a manner that in accordance with a developed feature of the invention, a specimen is first reduced in size flatly, to a relatively thin layer, that on this plane specimen-surface, a carrier slide is cemented, and the latter together with the specimen is rotated 180°, following which, a further removal of material takes place from the opposite side of the specimen, to a layer-thickness permissible for the microscopic investigation in transmitted light.

In contrast to the known techniques of cross-cutting or surface grinding with subsequent polishing of the specimen surface, the latter is achieved by the method according to the invention, by milling, in conjunction with which, on the one hand, surface qualities in the milling process are achieved which heretofore were not deemed possible, and subsequent laborious treatment can be dispensed with, and on the other hand, the slide preparation of even the hardest objects can take place within the shortest possible time.

In comprehensive test sequences with the different specimens, even with those having pronounced hardness-differences in the prepared specimen surface, very good results could be obtained, from the standpoint of technical preparation of a mirror-smooth and most extensively roughness-free possible specimen surface. In comparison to traditional specimen preparation by surface-grinding and subsequent polishing of the surface, the following outstanding advantages can be specified:

1. Great rapidity of the specimen preparation, in conjunction with which, in many cases, any subsequent treatment of the specimen surface can be dispensed with;

2. Where adequate characteristic hardness of the specimen materials is present, there is no need for object embedding, even where smaller objects are concerned;

3. Pores and cavities in the material of the specimen object, in contrast to traditional polishing, are not clogged and contaminated by polishing compound;

4. In multiphase systems, phases of differential hardnesses are removed with a uniform degree, avoiding compressions and deformations by squeezing, in an object range exhibiting only a rather slight hardness;

5. For three-dimensional demonstration of the microstructures, bevelled edges can be prepared without trouble, under known angles; and 6. When using diamond milling, success is achieved even in hard objects (such as metal surfaces) in the preparation of the specimen surface even for electron scan microscope and X-Ray analytical studies, in a working operation without any subsequent treatment.

The method proposed in accordance with the invention thus proves itself to be superior both to known techniques of preparation, as well as in any aspect.

DESCRIPTION OF THE PREFERRED EMBODIMENT

With reference to the device to be provided for the preparation of specimen surfaces, the task before us is resolved in such a manner that a milling unit equipped with a revolving milling head for area removal of material from the specimen is coordinated with a slide taking in the object to be prepared in a manner known in itself, in a frame, and that slide and/or milling unit can be blocked to each other on at least one plane.

An appropriate form of improvement of the device proposed can be characterized in such a way, that the slide is received from guideways running in a plane parallel to the cutting level of the milling head. The arrangement of the milling head, in so doing, can be contrived in such a manner that the latter rotates in a horizontal plane with cutting edges arranged on the underside.

An especially simple improvement occurs if, in accordance with a further feature of the invention, the milling head is placed directly on the shaft of the driving motor of the milling unit.

A further advantageous feature of the invention consists in the fact the milling unit is coordinated with a microtome, known in itself, with horizontally controlled slide in place of the regular knife holder.

Further details, advantages and specialities of the invention will be clarified, reference being made to the exemplifications of the device proposed here, demonstrated in perspective and schematically, in the attached drawing.

In the milling apparatus, designated by 10 in its entirety, there is disclosed, as far as the basic assembly is concerned, of a microtome known in the art with a slide 12 slidably disposed in a horizontal slideway 11, the drive of which slide takes place in a known manner. Driving of slide 12 may be through gear unit 13 and corresponding thrust elements, derived from a driving means which likewise is well known in the art. Coordinated to the slide is a specimen clip 14 in which the object specimen 15 is clamped in a known manner.

On the support or stand 16 of the device, and clear over to the slideway 11, a bridge 17 overextending the latter is arranged, to the central section 18 of which, the milling unit 20 is attached, which extends essentially vertically upwards over the slideway. This central section 18 of the bridge 17, in microtomes of traditional construction type, accepts the knife holder and is provided with corresponding means for adjustment and/or knife adjustment to the object specimen, which here, however, is not of further interest.

The milling head possesses a driving motor 21 with vertically rotating motor shaft 22, which extends downward away from the motor, and carries on its free end the milling head 23, with cutting edges 24, 25 arranged on the underside. The cutting edges thus rotate in a horizontal plane, and remove material from the object specimen 15 on the surface 26, brought into their operating area by means of the slide 12 with predetermined speed of thrust or feed. After a sweep of the specimen, the preparation of the specimen surface 26 is completed.

The remaining elements of the device, shown in the drawing, are held in the usual framework of microtomes, and do not require further discussion here.

Preparations affected with a device according to the exemplification of the invention clarified above, have confirmed the superiority of the proposed method in the most varied types of object specimen materials in comparison to other slide preparation techniques. This can be clarified, reference being made to the following experimental results.

In polyamide bristles embedded in a polyester casting-resin mounting medium as object specimen, the quality condition of a surface prepared through cross-cutting with a microtome knife, through polishing, and through milling of the same specimen, was compared with each other. Whereas after the conclusion of the polishing procedure, the polyamide bristles protruded from the surface of the casting-resin block, bristles and casting-resin mounting medium were removed to the same degree after the cross-cutting and the milling. The roughness of the specimen surface obtained by cross-cutting was appreciably greater than that of the milled surface.

The shell of a Brazil nut served as the specimen for a further experiment. In a cross-section through the shell, a completely roughness-free and smooth surface formation was shown in the milled surface, whereas in the specimen surface obtained by cross-cutting, small specimen-parts of the shell were compressed and also individually pulled out. A longitudinal section through the shell of the Brazil nut essentially led to the same results, in which the differences between the surfaces obtained by milling over, and cross-cutting clearly stood out especially because not only in the last-mentioned instance in the shell alone, compressions were also recognizable in the inner and outer araldite casting-resin surfaces.

In a further experiment, a ceramic-like filling compound was present, as an especially hard object, between miltilayered aluminum foils. Through milling, an extensively smooth and artifact-free surface was produced. After the cross-cutting, clear roughnesses, compressions and smearings were shown on the cross-sectional surfaces of the aluminum foils. Also on the surface of the ceramic substance, a plugging of the pores and of the diagonally-coursing seam was recognizable.

Depending on the materials of the specimens to be prepared, hard metal millers or diamond millers can be utilized within the scope of the present invention.

We claim:
1. A method of preparing a thin specimen section in a microtome having a rotary milling cutter for microscopic studies in a transmitted light microscope comprising mounting a specimen to be prepared for examination on the slide means of said microtome, advancing said specimen relatively toward said rotary milling cutter of said microtome in a plane parallel to the plane of said rotary milling cutter of said microtome, removing a predetermined thickness of material of said specimen by cutting by said rotary milling cutter thereby to achieve a mirror-smooth and roughness-free, flatly-reduced specimen surface, removing said specimen from said slide means, affixing said reduced surface to an examination slide holder, further mounting said specimen on said examination slide holder to said slide means of said microtome, advancing said specimen generally horizontally relatively toward said rotary milling cutter of said microtome, removing a predetermined thickness of material of said specimen by cutting by said rotary milling cutter thereby to achieve a specimen slide having a layer thickness which accommodates microscopic examination in transmitted light.

* * * * *